US010792381B2

(12) United States Patent
Poulsen (10) Patent No.: US 10,792,381 B2
(45) Date of Patent: Oct. 6, 2020

(54) SYSTEM FOR DISINFECTING SURFACES USING ULTRAVIOLET LIGHT

(71) Applicant: Bridgeport Magnetics Group, Inc., Shelton, CT (US)

(72) Inventor: Peder Ulrik Poulsen, Shelton, CT (US)

(*) Notice: Subject to any disclaimer, the term of this patent is extended or adjusted under 35 U.S.C. 154(b) by 0 days.

(21) Appl. No.: 16/366,350

(22) Filed: Mar. 27, 2019

(65) Prior Publication Data

US 2019/0298869 A1 Oct. 3, 2019

Related U.S. Application Data

(60) Provisional application No. 62/761,601, filed on Mar. 29, 2018.

(51) Int. Cl.
| | |
|---|---|
| *A61L 2/10* | (2006.01) |
| *A61L 2/24* | (2006.01) |
| *A61L 2/28* | (2006.01) |
| *F21V 21/15* | (2006.01) |
| *F21S 8/06* | (2006.01) |
| *H05B 47/105* | (2020.01) |

(52) U.S. Cl.
CPC ........ *A61L 2/10* (2013.01); *A61L 2/24* (2013.01); *A61L 2/28* (2013.01); *F21S 8/063* (2013.01); *F21V 21/15* (2013.01); *H05B 47/105* (2020.01); *A61L 2202/11* (2013.01); *A61L 2202/14* (2013.01); *A61L 2202/16* (2013.01); *A61L 2202/25* (2013.01)

(58) Field of Classification Search
CPC ..... A61L 2/10; A61L 2/24; A61L 2/28; A61L 2202/11; A61L 2202/14; A61L 2202/16; A61L 2202/25; F21S 8/063; F21V 21/15; H05B 47/105

USPC .......................................................... 362/272
See application file for complete search history.

(56) References Cited

U.S. PATENT DOCUMENTS

| | | | |
|---|---|---|---|
| 6,242,753 B1 | 6/2001 | Sakurai | |
| 8,067,750 B2 | 11/2011 | Deal | |
| 8,350,228 B2 | 1/2013 | Welker | |
| 8,569,715 B1 * | 10/2013 | Tantillo | ..................... A61L 2/10 250/453.11 |
| 8,770,949 B2 | 7/2014 | Noble | |

(Continued)

FOREIGN PATENT DOCUMENTS

| | | |
|---|---|---|
| CN | 201237182 Y | 5/2009 |
| CN | 201921150 U | 8/2011 |

(Continued)

OTHER PUBLICATIONS

Wei Luo, et al., "Comparison of sterilization efficiency of pulsed and continuous UV light using tunable frequency UV ystem", Innovative Food Science & Emerging Technologies, vol. 26, Dec. 2014, pp. 220-225 (3 page abstract only).

*Primary Examiner* — Cara E Rakowski
*Assistant Examiner* — Hana S Featherly
(74) *Attorney, Agent, or Firm* — St. Onge Steward Johnston & Reens, LLC (57) ABSTRACT

A surface disinfecting system utilizing UV radiation emitted from at least on UV lamp, the UV lamp positioned in a light fixture that is positioned in a room to be disinfected. The light fixture is provided with a shaft upon which the light fixture rotates according to a predetermined cycle. The cycle may be programmed to adjust the speed and direction of rotation and intensity of the UV lamps.

28 Claims, 6 Drawing Sheets

(56) References Cited

U.S. PATENT DOCUMENTS

| | | |
|---|---|---|
| 8,907,304 B2 | 12/2014 | Kreitenberg |
| 9,358,313 B2 | 6/2016 | Deal |
| 9,370,600 B1 | 6/2016 | DuPuis et al. |
| 9,700,072 B2 | 7/2017 | Dobrinsky et al. |
| 9,889,219 B2 | 2/2018 | Dayton |
| 2008/0253941 A1 | 10/2008 | Wichers et al. |
| 2009/0129974 A1 | 5/2009 | McEllen |
| 2011/0054574 A1 | 3/2011 | Felix |
| 2016/0271803 A1 | 9/2016 | Stewart |
| 2017/0100500 A1 | 4/2017 | Garner et al. |
| 2018/0193501 A1 | 7/2018 | Ufkes |
| 2018/0193502 A1 | 7/2018 | Ufkes |

FOREIGN PATENT DOCUMENTS

| | | |
|---|---|---|
| CN | 203874137 U | 10/2014 |
| CN | 204072835 U | 1/2015 |
| CN | 204501798 U | 7/2015 |
| CN | 107837408 A | 3/2018 |
| KR | 200315033 Y1 | 6/2003 |

\* cited by examiner

SYSTEM FOR DISINFECTING SURFACES USING ULTRAVIOLET LIGHT

FIELD OF THE INVENTION

The invention relates to disinfectant systems and more specifically, to a single source ultraviolet light emitting assembly for disinfecting surfaces within health-care venues such as patient rooms, clinics, operating rooms, endoscopy suites, as well as food processing facilities and the like.

BACKGROUND OF THE INVENTION

The growing problem of bacterial resistance to antibiotics is causing a global rise in the incidence of Hospital-Associated Infections (HAI). A recent study by the Center for Disease Control and Prevention (CDC) showed that in the United States during 2016, HAIs affected 5-10% of hospitalized patients. Approximately 1.7 million HAIs occurred resulting in 99,000 deaths and an estimated $20 billion in healthcare costs.

Surfaces in hospital rooms are continually being contaminated with infectious pathogens such as Methicillin-resistant *Staphylococcus aureus* (MRSA), vancomycin-resistant *Enterococcus* (VRE), *Clostridium difficile* (C-diff) and others. These infectious pathogens are transmitted to surfaces by individuals with contaminated hands and clothing, contaminated instruments, items that are brought in and out of the room such as personal and hospital issued mobile devices or from the patients themselves. In addition, in some instances the air entering the room is not sterile and deposits pathogens carried by dust and aerosols onto surfaces.

Despite rigorous manual cleaning, pathogens from previous occupants may also survive and potentially infect a next patient who is brought into the room.

In response to the rise in HAIs, some companies are now offering Ultraviolet Light (UV-C) based transportable disinfection devices for supplementing manual room cleaning. These devices are brought into the room and turned on, nominally disinfecting relevant surfaces in 15-20 minutes. The process must be carried out while the room is vacant due to the hazards of UV-C radiation to unprotected eyes and is normally performed after manual chemical cleaning.

These devices generally feature multiple UV-C emitting tubular lamps mounted vertically onto a wheeled base which is positioned centrally in the room. Low pressure tubular mercury lamps can be effective for germicide purposes because they emit two narrow peak wavelengths of 185 nm and 254 nm where the latter peak is close to the wavelength where DNA and RNA exhibit maximum ultraviolet absorption.

The fluence level (a time-integrated flux describing the energy delivered per square cm of surface area) is relative to the distance of a surface from the UV source. The time required to deliver a typical bactericidal dose of about 30 mJ/cm2 depends on the lamp power, the angle of approach and the presence of objects which may block the line of sight to the source. A relatively short cycle time is important because the process must take place during the absence of patients and staff due to the harmful effects of intense UV radiation and in order to increase the room turnaround rate in a medical facility.

In some installations, UV lighting fixtures have been permanently installed onto the ceiling of certain spaces (e.g. an operating room) and are activated between procedures. The number and wattage of stationary fixtures can depend on the size of the room and the placement of equipment and furniture to be sterilized.

The majority of systems being offered (Steris-Pathogen, Lumalier, American Air-ARTZ, Clorox-Optimum, UV-C Technologies, Xenex, and others are transportable. The units are moved manually into patient rooms, IC rooms and treatment rooms with known risk of infection. They are mostly single source systems which must be relocated in between cycles in order to effect full coverage of a room. One system includes three column shaped sources meant to be placed strategically in order to reduce distances and minimize shadows. However, the staff must be trained in moving and operating the systems, often working around the clock, in order to amortize the capital investment and to achieve faster room turnover rates.

All of the above described systems, whether light fixtures installed in the ceiling or portable lighting stands that are moved into and positioned in a space, unfortunately rely at least partially on reflection of the UV light from walls and ceilings in the space for full treatment of surfaces blocked from line of sight.

SUMMARY OF THE INVENTION

What is desired then is a system and method for disinfecting the surfaces in a space that more efficiently and more effectively kills bacteria.

It is also desired to provide a system and method for disinfecting surfaces in a room with UV light that more effectively prevents HAIs.

It is further desired to provide a system and method for disinfecting surfaces in a room automatically with reduction of the negative effects of shadowing due to surfaces being blocked from line of sight to the disinfecting UV light source.

It is still further desired to provide a system and method for effectively disinfecting surfaces in a room that does not require specific or detailed training for personal to operate.

These and other benefits are achieved in one configuration by the provision of a surface disinfection system comprising one or a plurality of ultraviolet light emitting fixtures and a control interface for controlling the system. In one configuration it is contemplated that the UV light fixtures may be oriented in a horizontal plane and extend radially from a central vertical column, which may be affixed to the ceiling. In another configuration, it is contemplated that the system may be affixed to the floor or may comprise a transportable wheeled base that can be moved into a space to be treated. In particular, a motorized controllable rotator enables the fixture to rotate around an axis defined by the vertical column. Each fixture may include one or a plurality of UV lamps and ballasts for lamp power supply. Additionally, a disinfection cycle may be programmed into the system and could comprise one or several slow full or partial revolutions of the system. The rotation serves to distribute the UV radiation evenly and minimize shadows throughout the space.

It is contemplated that the system could be provided as a UV-C surface sterilizing system designed primarily for permanent installation in patient rooms, intensive care units, emergency units, operating rooms and other venues presenting a high risk of infections.

The UV light source could comprise light fixture (e.g., up to 8 feet in length), which is suspended from the ceiling by a single column terminated in a set of bearings, which could be located about 2 feet from the end. A motor and reduction gear may serve to rotate the assembly relatively slowly in a horizontal plane about 7 feet above the floor. A sterilization cycle may be performed in the course of two full revolutions, (e.g., first clockwise and then counterclockwise, returning the unit to the starting point). In one configuration, a (sliding) hinged panel in front of the lamps may (move backward) open automatically to expose the lamps at the start and may then close at the end of the cycle.

The UV-C emitters (high intensity mercury amalgam lamps or UV LEDs) and reflector could be mounted on the underside of the (6 foot long) section opposite the drive end. When energized, due to the slow, barely visibly noticeable, rotation, all objects within the room will receive germicidal UV light from varying directions. In this manner, even if there are objects that may create a shadow on a surface to be sterilized, the rotation of the light source will ensure that the surface is properly sterilized.

The efficacy of the system described above exceeds that of vertical, column based systems. The horizontal facing of the light sources (the elongated lamps) enables an improved angle of approach to most critical target surfaces. For example, the distribution of UV light onto a flat surface such as a counter top, will be better from a horizontally mounted light source than a vertically mounted light source. This is because the light from the horizontally mounted light source will strike the surface at close to a perpendicular angle.

Horizontally mounted light sources also ensure that the vertical distance from the light fixture to beds, bedding, table tops, chairs and equipment is minimized, typically not exceeding four to six (4-6) feet. This ensures a higher amount of energy is transferred to the surface to be disinfected.

Additionally, most surfaces which would be shaded from a stationary emitter are opened to a direct line of sight due to the rotating (moving) nature of the UV-C light source.

It should further be noted that dosing can be customized to suit the particular room and furniture set up by means of programmed stops at selected angles during the sweep. For example, the system could be programmed to stop (e.g., for a full minute or longer) in front of an open bathroom door to thoroughly flood the location, or stop for a programmed time frame at other areas deemed critical or more likely to be supporting bacteria. This feature is also useful in order to provide coverage in an elongated room. For example, if one fixture is being utilized in the space, the rotation of the device at certain angles, corresponding with longer sections of the room, could be slowed to increase the amount of radiation transmitted to surfaces at a further distance.

When the system is permanently installed (e.g., the ceiling mounted embodiment), a customized cycle may be programmed and then duplicated again and again, eliminating the need for remote UV-C dosing sensors.

Another benefit to the current system is that is does not require trained staff to operate it properly. This is due to the fact that the system rotates and can be run via a program that may be designed specifically with the space in mind. Nor does the current system need complicated logistics to suit patient rotation as the system could simply be initiated when a patient vacates the room. Likewise, the permanently mounted type system does not require storage space between uses.

For this application the following terms and definitions shall apply:

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, applications, media, components, networks, systems, subsystems, and/or means, constituting any one or more of (a) a connection, whether direct or through one or more other devices, apparatus, files, programs, applications, media, components, networks, systems, subsystems, or means, (b) a communications relationship, whether direct or through one or more other devices, apparatus, files, programs, applications, media, components, networks, systems, subsystems, or means, and/or (c) a functional relationship in which the operation of any one or more devices, apparatus, files, programs, applications, media, components, networks, systems, subsystems, or means depends, in whole or in part, on the operation of any one or more others thereof.

In one configuration a light fixture adapted to disinfect surfaces is provided, the light fixture comprising: a base, a shaft coupled to the base, and an enclosure coupled to the shaft. The light fixture further comprises at least one ballast positioned in the enclosure, the at least one ballast adapted to be connected to a source of electrical power. The light fixture still further comprises at least one Ultraviolet (UV) lamp positioned in the enclosure and coupled to the at least on ballast, the at least one UV lamp adapted to emit radiation in a frequency that is harmful to bacteria, and an electric motor positioned in the enclosure and adapted to rotate the enclosure about an axis.

In another configuration a method of disinfecting surfaces in a room with UV light fixture is provided comprising the steps of coupling a shaft to a base, coupling an enclosure to the shaft, and positioning an Ultraviolet (UV) lamp and an associated ballast in the enclosure. The method further comprises the steps of emitting UV light from the UV lamp into the room, rotating the enclosure about an axis of rotation with a motor positioned within the enclosure, and controlling the rotation via predetermined settings.

In still another configuration a light fixture adapted to disinfect surfaces is provided, the light fixture comprising an enclosure coupled to a shaft, where the shaft is coupled to a base. The light fixture further comprises a plurality of Ultraviolet (UV) lamps positioned in the enclosure and coupled to a source of electrical power, the UV lamps being adapted to emit radiation in a frequency that is harmful to bacteria. The light fixture still further comprises an electric motor positioned in the enclosure and adapted to rotate the enclosure in a horizontal plane around an axis of the shaft, and an interface adapted to operate the light fixture.

Other objects of the invention and its particular features and advantages will become more apparent from consideration of the following drawings and accompanying detailed description.

DETAILED DESCRIPTION OF THE INVENTION

Referring now to the drawings, wherein like reference numerals designate corresponding structure throughout the views.

Figure 1:
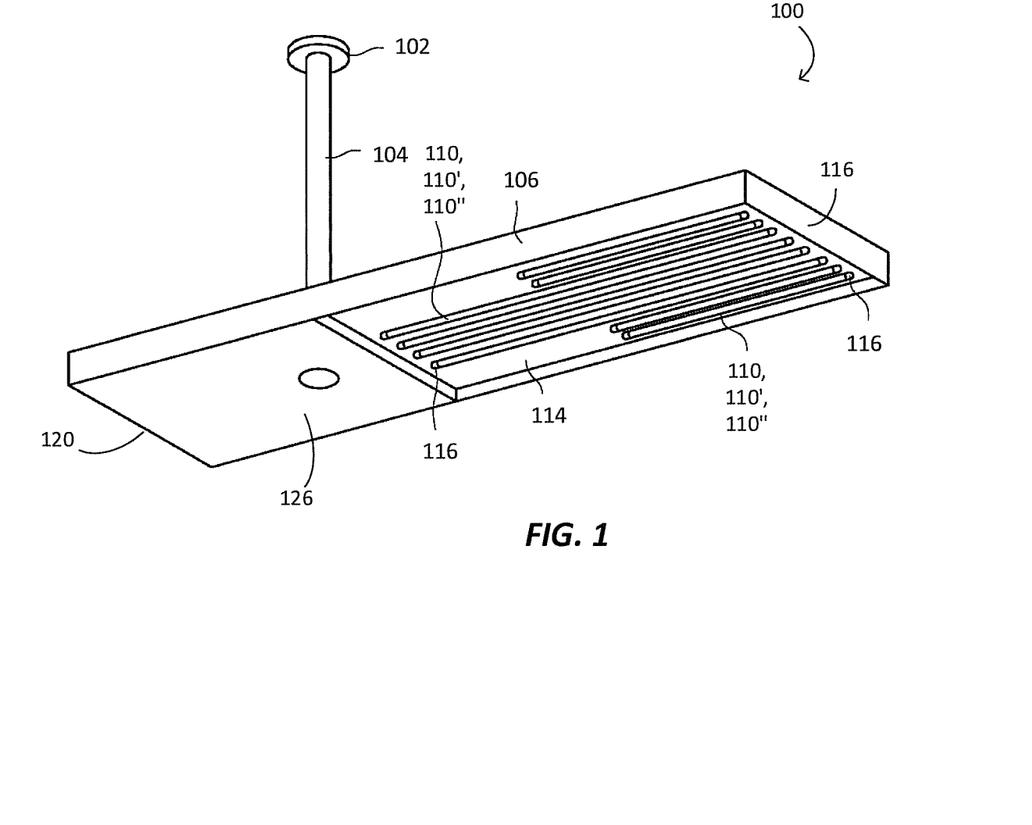
FIG. 1 is a perspective view of one configuration of an UV light fixture according to an embodiment of the invention.
Figure 2:
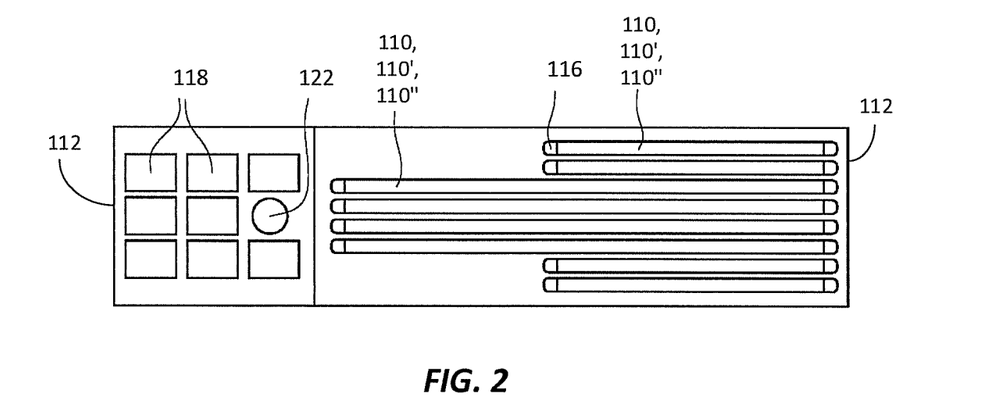
FIG. 2 is another view of the light fixture according to FIG. 1.

FIGS. 1 and 2 are depictions of one configuration of a UV light fixture 100 that may be provided with a base 102 coupled to a shaft 104. The UV light fixture is provided with an enclosure 106 that may be an elongated housing. In one configuration, the enclosure 106 may be up to eight (8) feet in length. The enclosure 106 is provided with a cavity 108 within which UV lamps (110, 110', 110") are positioned. The cavity may be positioned toward one end 112 of enclosure 106. The enclosure 106 may further be provided with a reflective surface 114 which functions to reflect radiation from the UV lamps (110, 110', 110") outward into the space in which the UV light fixture 100 is positioned.

The UV lamps (110, 110', 110") may be selected to be tubular elongated lamps that may be fit into standard lamp sockets 116 positioned within the enclosure 106. The UV lamps (110, 110', 110") may be oriented in parallel with each other and in one configuration, could be provided having differing lengths.

A plurality of ballasts 118, 118', 118") are shown toward a second end 120 of enclosure 106. In the example shown in FIG. 2, there are eight ballasts shown, however it should be understood that fewer or more may be used as needed depending on the configuration of the UV lamps used for the light fixture 100.

Also shown in FIG. 2 is an drive motor 122 that is positioned in the enclosure 106. The electric motor may further be provided with a reduction gear 124 (FIG. 6), which serves to rotate the fixture in a horizontal plane around the axis defined by the shaft 104. The shaft 104 is used to support the light fixture 100. In one configuration, the shaft is immovably fixed relative to the enclosure 106 and rotate relative to the base 102 via bearing (not shown).

Figure 3:
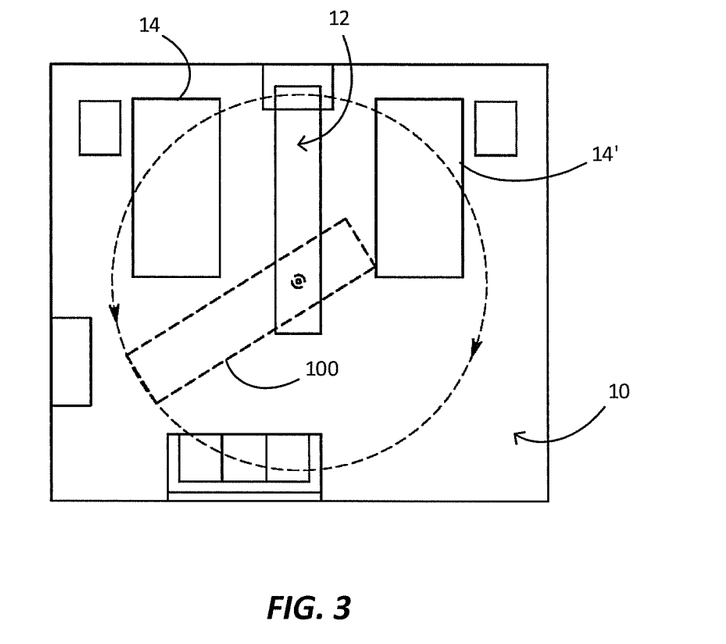
FIG. 3 is a view of the light fixture according to FIG. 1 installed in the ceiling of a room illustrating the rotation of the light fixture about an axis.
Figure 4:
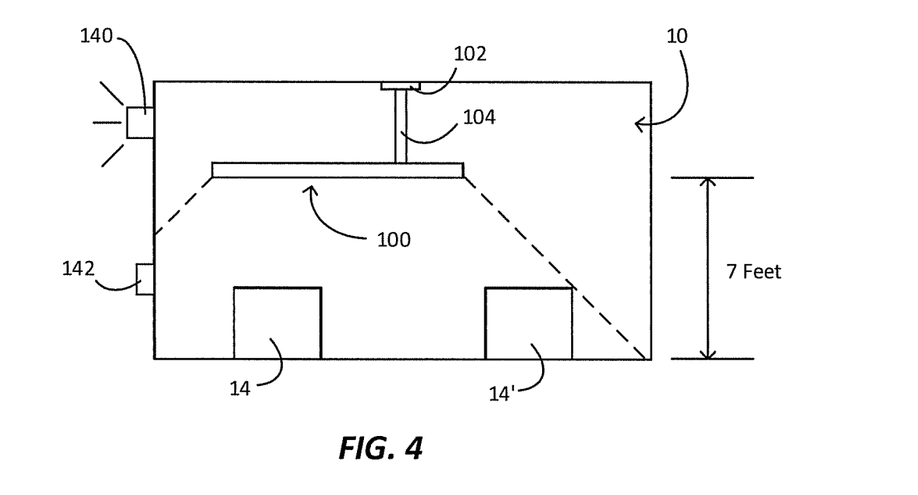
FIG. 4 is a side view of the configuration according to FIG. 3.

FIGS. 3 and 4 depict the light fixture 100 installed centrally in a patient room 10. The lower surface 126 may be positioned at about 7 feet above the floor and when not in use the light fixture 100 may be rotated to a position out of the way at a midpoint 12 between the two beds (14, 14'). A typical sterilization cycle may turn the UV light fixture 100 on for approximately 10 minutes during which period, the light fixture 100 is rotated. In one configuration, the light fixture could be programmed to rotate 360 degrees in a first direction (e.g., clockwise) over a five minute period, and then rotate 360 degrees in a second direction (e.g., counter-clockwise) over a second five minute period. Essentially, the cycle could end with the unit returned to the original parked position at midpoint 12 between the two beds (14, 14').

Dashed lines are provided (FIG. 4) to illustrate the dispersion of UV light emitted from the UV lamps 110 throughout the space during the cycle.

It should be noted that the efficiency of the light fixture 100 in killing bacteria exceeds that of stationary and/or vertically oriented systems for several reasons. The orientation of the UV lamps (110, 110', 110") is provided in a horizontal plane relative to most important target surfaces. The vertical distance from bedding, bed table tops and other furniture is minimized and most surfaces, which would be shaded from a stationary source, will be exposed to a direct line of sight due to the slowly moving UV source during a part of the cycle. This translates into the delivery of a sufficient amount of radiation to target surfaces, which in turn, requires considerably lower power and fewer number of lamps than would otherwise be needed. Another benefit of the current configuration of the invention is that effective sterilization can be accomplished largely by duplicating a cycle that has been proven effective. This then eliminates the need for complicated calculations and/or remote UV-C sensors. Another important benefit from the proposed configuration is that it would no longer be necessary for staff to move, relocate and operate the light fixture 100. This will eliminate the need to provide extensive training for the staff as the light fixture can operate in a predetermined manner once activated.

Figure 5:
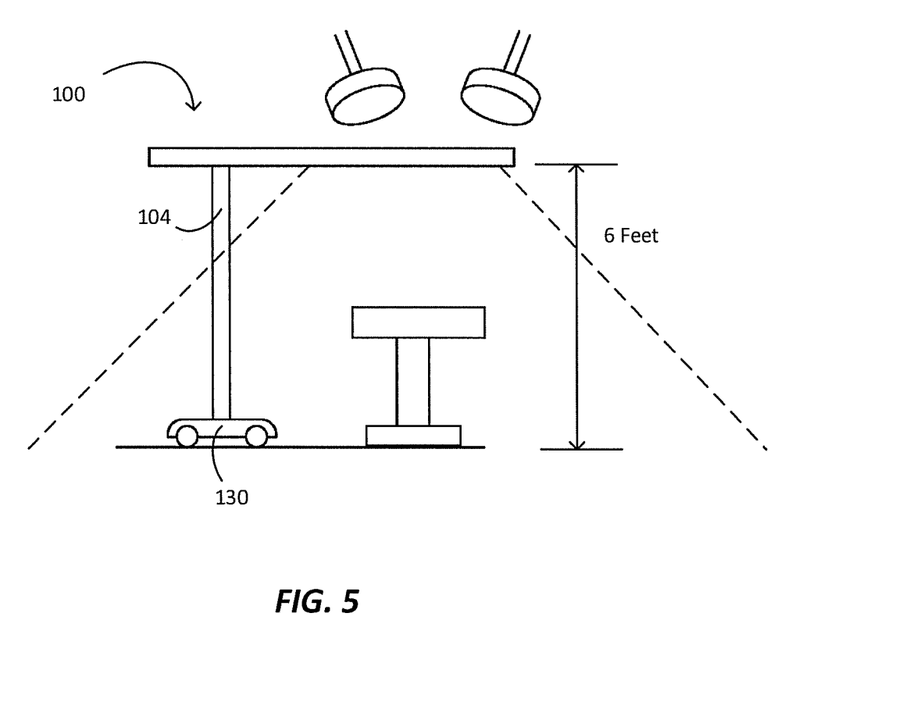
FIG. 5 is a portable UV light fixture according to another configuration of the invention featuring a column mounted upon a wheeled base.

It is understood, however, that some venues may not be amenable to the installation of a permanent UV light fixture 100. For example, an operating room or suite may have tight space constraints due to location of equipment including lighting and imaging equipment. Additionally, some venues that require a variety of steps ups to accommodate different procedures may need to keep overhead space free. In these types of room configurations, a portable UV lighting fixture 100 may be provided as shown in FIG. 5. In this configuration, the light fixture 100 is mounted onto a wheeled base 130, which can be moved into an area to be treated. For example, in this configuration the light fixture 100 may be moved into a space and positioned close to the most important targets to be treated. This portable version of the light fixture 100 may comprise the same UV light emitting features as previously described in connection with FIGS. 1-4. However, in this configuration shaft 102 is provided with a flange (not shown) to the underside of the rotator and is mounted upon wheeled base 130. Additionally, the horizontally mounted light fixture 100 may be positioned at about 6 feet above the floor, which is low enough to easily pass through doors and below overhead lights, but still close enough to the operating table and instrument tables to deliver a sufficient dose of radiation during one or several 360 degree sweeps of the area.

Figure 6:
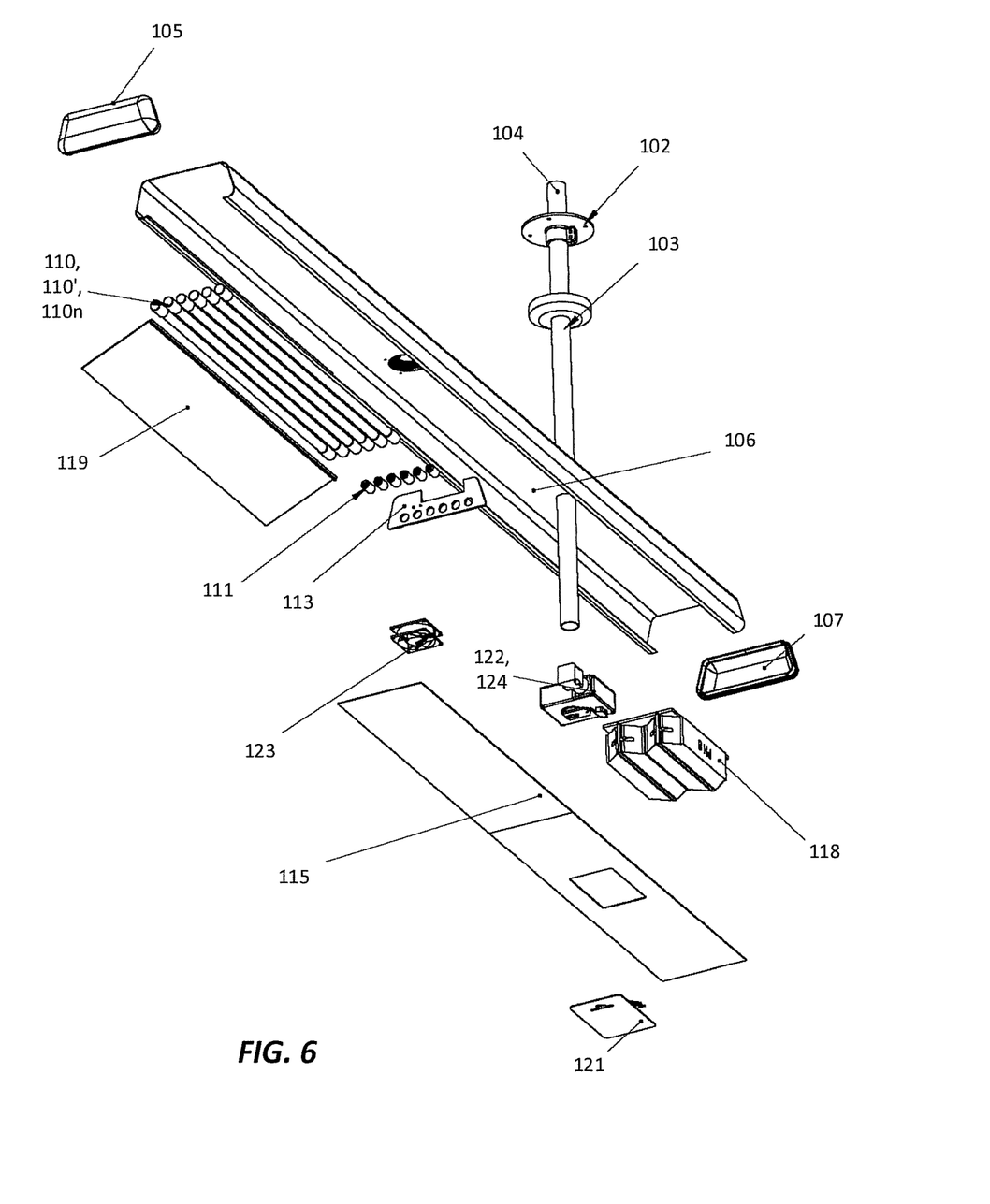
FIG. 6 is an exploded view of the configuration according to FIG. 1.
Figure 7:
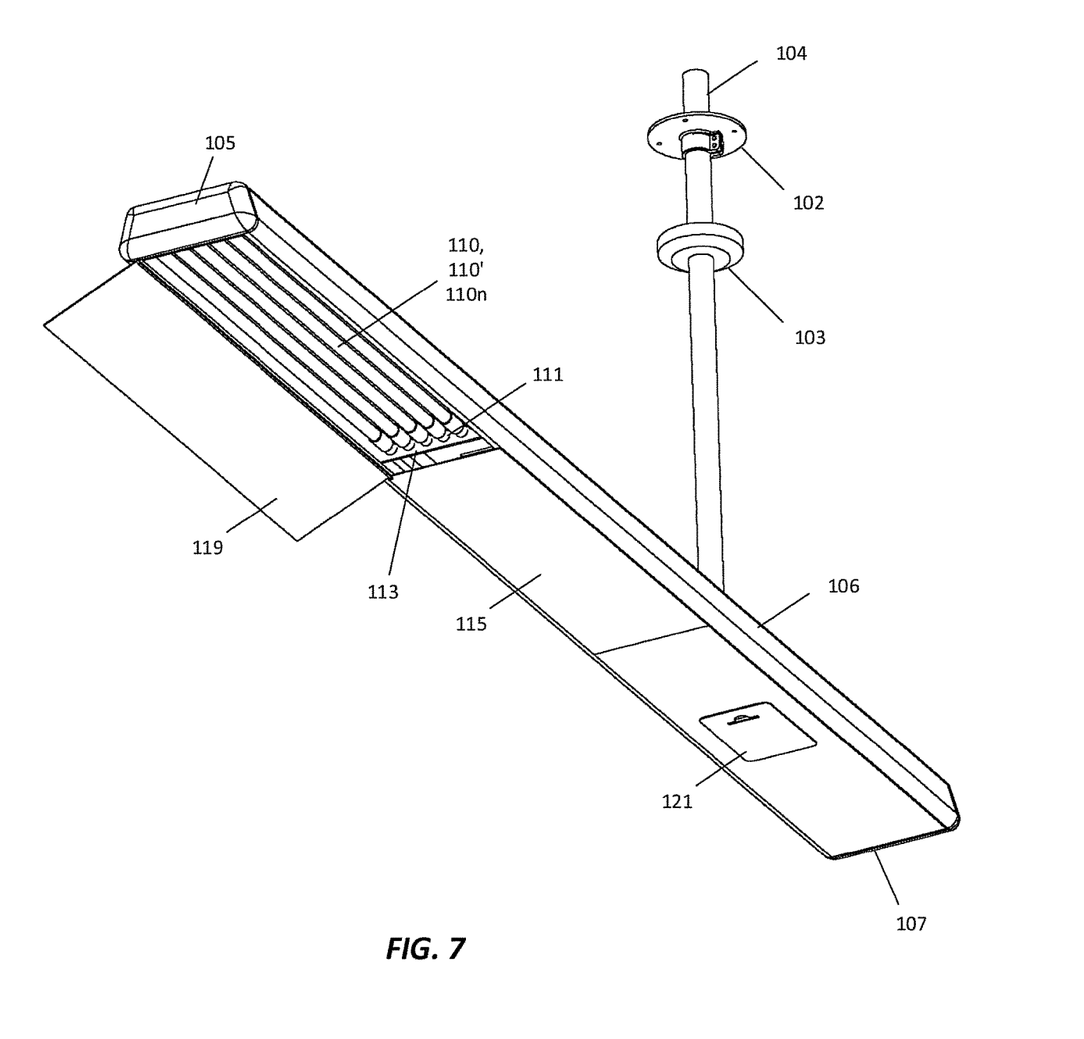
FIG. 7 is an assembled view of the configuration according to FIG. 6.

Turning now to FIGS. 6 and 7, another configuration of the light fixture 100 is provided where FIG. 6 is an exploded view of the components of the assembled light fixture 100 depicted in FIG. 7.

The light fixture 100 that is illustrated in FIGS. 6 and 7 is similar to that shown in connection with FIG. 1 with slightly different dimensions and a few additional features. For example, as can be seen in FIG. 7 the UV lamps (110, 110', 110n) are all of a single length and extend a shorter length relative to the total length of enclosure 106.

Looking at the exploded view in FIG. 6, the light fixture 100 comprises a base 102 coupled to a shaft 104 along with a cover mount 103 for the shaft 104. An enclosure 106 is shown coupled to the shaft 104 where the enclosure is provided with a first end cap 105 and a second end cap 107.

The shaft 104 engages with drive motor 122, which includes reduction gear 124. The UV lamps (110, 110', 110") are supported by sockets 111 and a fire wall socket mount 113 is also shown. The UV lamps (110, 110', 110") are coupled to ballast 118, which is designed to provide electrical power of the correct voltage and frequency to UV lamps (110, 110', 110"). A cover 115 is further provided, which is designed to enclose the drive motor 122, the ballast 118 and any wiring residing in enclosure 106. An opening 117 is provided in cover 115 into which an SD card reader assembly 121 may be inserted. Also shown is a hinged cover 119 that is provided to open allowing access to the UV lamps (110, 110', 110"). The hinged cover 119 is designed to open and close and may, in one configuration, be automated to open during a cycle and automatically close when the cycle is completed. Also provided is fan 123 that may be coupled to or include and integral a temperature sensor for maintaining the temperature in the light fixture 100 during operation.

Looking at the overall design of the light fixture 100, it is important to recognize that several factors contribute to the efficacy of the process.

Distance.

The intensity of radiation falls off exponentially with the distance from the source. Accordingly, the horizontal mounting of the UV lamps (110, 110', 110") allows for the minimum distance to be achieved from the lamp to the surface to be disinfected. This in turn, allows for less power to be consumed and for a quicker cycle of disinfection.

Angle of Approach.

There are horizontal high touch areas and include, desk tops, table tops, chairs, beds, bed tables and bedding surfaces that must receive an adequate dose of radiation. Alternatively, walls and ceilings are contacted by persons much less frequently. Most know UV emitters utilize columns or banks of vertically mounted UV tubes that are centered in a plane approximately 3-4 feet above the floor. This means that a majority of the radiation emanating from these sources will reach a horizontal surface at an oblique angle ranging from between 15 and 30 degrees. This oblique angle means that a much lower amount of radiation will be transferred to the surface to be disinfected. In fact, at a 30 degree angle a surface receives only about half of the amount of energy than radiation striking the surface essentially perpendicular. Likewise, radiation traveling largely parallel to the surface provides almost no energy transfer to the surface.

Shadows.

Another area of concern for disinfecting UV light fixtures are the creation of radiation "shadows", which are areas that are behind an obstruction meaning there is no direct line of sight from the surface to the UV light source. The areas that are cut off from a direct line of sight to the UV light source by, for example equipment and/or other objects, thus rely on reflection from walls. However, this means the distance the radiation must travel is greatly increased, which in turn, means that the energy level transfer of the radiation falls off exponentially.

It is further understood that UV-C radiation can cause damage to individuals that are exposed to the radiation including damage to eyes and skin. As such, UV surface sterilization should be performed without persons in the room. In one configuration, a visual indication 140 (FIG. 4) is provided outside of the room that is being disinfected providing an indication to personnel to not enter the space until the cycle is completed.

The light fixture 100 may, in one configuration, be controlled by an interface 142, which could comprise a switch, or a RFID card reader or key-pad (FIGS. 4 & 8) installed outside the room next to the entrance. The cleaning staff could be issued numbered RFID cards to start the sweep by holding their card up to the card reader. The system can be configured to capture use data (operator identity, date and time, and system status) which could be stored on the SD card reader 121.

In one configuration, when the system is activated by an RFID card, the following actions occur: 1) A green LED signals that the card code is received and accepted. 2) A flashing amber light next to the panel signals that a sweep is in progress. 3) A timing circuit starts counting down 30-60 seconds to lamps on. 4) The panel in front of the lamps is retracted. 5) A second timer allows 1 minute warm up for lamps to reach full output. 6) The UV light fixture starts a customized sweep featuring programmed stop angles and dwell times. A loud interrupted-tone buzzer signals that a sweep is ongoing.

The UV light fixture 100 could also be provided with an on board proximity sensor that interrupts the process if a person is detected in the room. Additionally, a door sensor can be used to monitor if the door is opened, which could function to interrupt the cycle while the door is open. Upon closing of the door, the cycle can pick up where it was paused and continue to completion.

The light fixture could be built according to the following specifications: 1) Supply voltage 120V or 230V, 50/60 Hz; 2) Input power 1,100 watts; 3) Output, UV-C radiation app. 350 watts; 4) Sweep circle diameter 12 ft. (366 cm); 5) Area coverage, typically 400-500 sq.ft.; 6) UV-C dose, horizontal surfaces >50 mWs/cm2 (20-min cycle) 7) Time/720 deg. Sweep 20 minutes+programmed stops.

The program for running the cycle can be room specific, cyclic programmed, where timed local pauses can be programmed to enhance dosing of critical areas as required.

Figure 8:
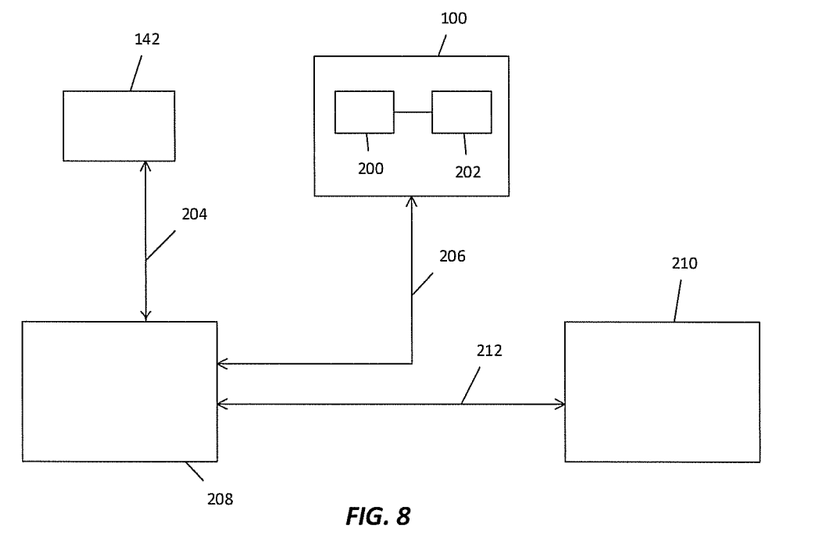
FIG. 8 is a block diagram of the light fixture according to FIG. 1 and further including various interconnected devices and systems.

Turning now to FIG. 8 a block diagram is illustrated depicting the light fixture 100 including a processor 200 and a storage 202. Also depicted in FIG. 8 is interface 142, which could comprise any of the devices and/or configurations previously described herein. Interface 142 is shown coupled to computer 208 via a connection 204, which could comprise in one configuration, a network connection. Additionally, computer 208 is shown connected to light fixture 100 via a network connection 206. While the various network connections are illustrated as wired connections, it is contemplated that wireless connections could effectively be used between the light fixture 100 and the interface 142 as well as the computer 208.

In this manner for a hospital setting, personnel at a computer station (e.g. nurses station) could remotely activate the cycle for sterilizing the room and be kept updated on the approximate time of completion on the computer screen. A visual indication 140 could be displaying a warning to any personnel in the area to not enter the room until the cycle has been completed. Alternatively, the interface 142 could be activated by personnel and provide a visual indication that the room is currently being sterilized. It should be noted that, even if the cycle is initiated by the interface 142, the process could still be followed and/or modified or halted remotely from computer 208. In this way maximum flexibility is provided for personnel in controlling the timing and manner of when a room is sterilized.

While the storage 202 is shown positioned in light fixture 100, it is further contemplated that this storage could be positioned in computer 208 or computer 208 could be provided with its own storage. In this manner, the programming of the light fixture 100 could be done from any or all of interface 142, SD card reader 121, computer 208 or computer 210. Likewise the operation and data collection on the cycles and maintenance could be remotely monitored by computer 208 or computer 210.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for disinfecting surfaces in a room comprising:
    a base;
    a shaft coupled to said base and having an axis of rotation;
    a mounting element coupled to said shaft, said mounting element having an upper surface and a lower surface;
    at least one ballast positioned on said mounting element, said at least one ballast adapted to be connected to a source of electrical power;
    at least one Ultraviolet (UV) lamp positioned on the lower surface of said mounting element and coupled to said at least on ballast, said at least one UV lamp adapted to emit radiation in a frequency that is harmful to bacteria;
    an electric motor positioned on said mounting element and adapted to rotate said UV lamp about the axis.

2. The system according to claim 1, wherein said mounting element further comprises an enclosure including a cavity having a reflective backing and said at least one UV lamp is mounted in the cavity.

3. The system according to claim 2, further comprising a door that is positioned to cover said cavity and is adapted to open to allow the radiation from said at least one UV lamp to exit from said cavity.

4. The system according to claim 1, wherein said at least one UV lamp comprises an elongated lamp that extends at least partially along a length of said mounting element.

5. The system according to claim 1, wherein said at least one UV lamp comprises a plurality of UV lamps.

6. The system according to claim 5, wherein said plurality of UV lamps comprise elongated lamps that extend at least partially along a length of said enclosure.

7. The system according to claim 6, wherein said plurality of elongated UV lamps comprise lamps having at least two different lengths.

8. The system according to claim 1, further comprising a reduction gear adapted to rotate the mounting element in a horizontal plane around the axis.

9. The system according to claim 1, further comprising a visual indication position outside of the room adapted to provide an indication that the light fixture is in operation.

10. The system according to claim 1, further comprising an interface adapted to operate the light fixture.

11. The system according to claim 10, wherein said interface is selected from the group consisting of: a switch, a card reader, a key pad and combinations thereof.

12. The system according to claim 1, further comprising a fan positioned on said mounting element.

13. The system according to claim 1, wherein said base comprises a portable frame adapted to sit on a floor to be positioned within a room.

14. A system for disinfecting surfaces in a room comprising:
    a base;
    a shaft coupled to said base;
    an enclosure coupled to said shaft;
    at least one ballast positioned in said enclosure, said at least one ballast adapted to be connected to a source of electrical power;
    at least one Ultraviolet (UV) lamp positioned in said enclosure and coupled to said at least on ballast, said at least one UV lamp adapted to emit radiation in a frequency that is harmful to bacteria;
    an electric motor positioned in said enclosure and adapted to rotate said enclosure about an axis;
    an interface adapted to operate the light fixture;
    a processor; and
    a storage accessible by said processor, said storage adapted to store a program for operating said UV lamp and said electric motor in a predetermined manner.

15. The system according to claim 14, wherein said base is adapted to be mounted to the ceiling of a room and the predetermined manner of operation is based on a configuration of the room.

16. The system according to claim 14, wherein the predetermined manner of operation comprises control operations selected from the group consisting of: a speed of rotation, a direction of rotation, a sequence of direction changes, a sequence of pauses, an intensity of the lamp and combinations thereof.

17. The system according to claim 14, further comprising a computer coupled to said processor via a network connection, wherein said processor is adapted to be programmed by said computer.

18. The system according to claim 14, further comprising a computer coupled to said processor via a network connection, wherein said storage is positioned in said computer and said system is adapted to be controlled by said computer.

19. The system according to claim 14, further comprising a sensor such that if movement is detected in the room, the UV lamp will cease emitting radiation.

20. The system according to claim 14, further comprising a door sensor such that if a door to access the room is detected as open, the UV lamp will cease emitting radiation.

21. A system for disinfecting surfaces comprising:
    an enclosure comprising a mounting element having an upper mounting surface and a lower mounting surface, said enclosure coupled to a shaft, where the shaft is coupled to a base;
    a plurality of Ultraviolet (UV) lamps positioned on said lower mounting surface and coupled to a source of electrical power, said UV lamps adapted to emit radiation in a frequency that is harmful to bacteria;
    an electric motor positioned in said enclosure and adapted to rotate said enclosure in a horizontal plane around an axis of said shaft; and
    an interface adapted to operate or program the system.

22. The system according to claim 21, wherein said interface is selected from the group consisting of: a switch, a card reader, a key pad and combinations thereof.

23. The system according to claim 21, further comprising:
    a processor; and
    a storage accessible by said processor, said storage adapted to store a program for operating the UV lamps and the electric motor in a predetermined manner.

24. The system according to claim 23, wherein the predetermined manner of operation is based on a configuration of the room.

25. The system according to claim 23, wherein the predetermined manner of operation comprises control operations selected from the group consisting of: a speed of rotation, a direction of rotation, a sequence of direction changes, a sequence of pauses, an intensity of the lamp and combinations thereof.

26. The system according to claim 23, further comprising a computer coupled to said processor via a network connection, wherein said processor is adapted to be programmed by said computer.

27. The system according to claim 23, further comprising a computer coupled to said processor via a network connection, wherein said storage is positioned in said computer and said system is adapted to be controlled by said computer.

28. The system according to claim 21, wherein the light fixture is positioned within a room and further comprising a visual indication position outside of the room adapted to provide an indication that the system is in operation.

* * * * *